United States Patent [19]

Undheim et al.

[11] 4,246,266
[45] Jan. 20, 1981

[54] ANTIMICROBIAL PYRIDTHIONES

[75] Inventors: Kjell Undheim, Blommenholm; Gunnar A. Ulsaker, Oslo, both of Norway

[73] Assignee: Nyegaard & Co. A/S, Oslo, Norway

[21] Appl. No.: 883,943

[22] Filed: Mar. 6, 1978

Related U.S. Application Data

[63] Continuation of Ser. No. 703,826, Jul. 9, 1976, abandoned.

[30] Foreign Application Priority Data

Jul. 10, 1975 [GB] United Kingdom ............... 29105/75

[51] Int. Cl.³ .................... C07D 213/04; A61K 31/44
[52] U.S. Cl. .................................. 424/263; 546/296; 546/114
[58] Field of Search ................. 260/294.8 T; 424/263; 546/296

[56] References Cited

FOREIGN PATENT DOCUMENTS 1190268  4/1970  United Kingdom ............. 260/294.8 T

OTHER PUBLICATIONS

Undheim et al., Acta Chemica Scandinavica, vol. 26, No. 6, pp. 2385-2400, (1972).
Hackh's Chemical Dictionary, McGraw-Hill Pub., Fourth Edition, p. 75, (1969).

Primary Examiner—Alan L. Rotman
Attorney, Agent, or Firm—Bacon & Thomas

[57] ABSTRACT

Antimicrobial compositions comprising as active ingredient at least one compound of the general formula

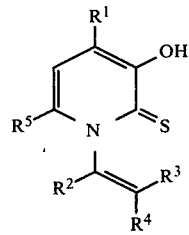

(wherein $R^1$ and $R^5$, which may be the same or different each represent a hydrogen or halogen atom and $R^2$, $R^3$ and $R^4$ which may be the same or different, each represent a hydrogen atom or a lower alkyl group) in association with an antimicrobial carrier, excipient or diluent. The compounds of formula I may be prepared by reacting a corresponding dihydrothiazolo 8-oxide compound with a base. Certain of the compounds of formula I are novel and may also be prepared by pyrolytic decarboxylation of a corresponding carboxyl substituted thiazolo-8-oxide compound.

32 Claims, No Drawings

ANTIMICROBIAL PYRIDTHIONES

This is a continuation of application Ser. No. 703,826, filed July 9, 1976 now abandoned.

This invention relates to antimicrobial compositions for use in medicine and in agriculture.

We have found that certain pyridthiones possess interesting activity against dermatophytes coupled with a freedom from neurotoxicity or any tendency to cause skin irritation or sensitisation. The activity of the above-mentioned pyridthiones against plant fungi also enables these compounds to be formulated into agricultural compositions for use, for example, against mildew.

According to the present invention there are thus provided antimicrobial compositions comprising as active ingredient at least one compound of the general formula

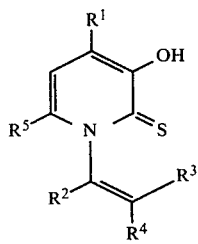

(I)

(wherein $R^1$ and $R^5$, which may be the same or different each represent a hydrogen or halogen atom and $R^2$, $R^3$ and $R^4$ which may be the same or different, each represent a hydrogen atom or a lower alkyl group) in association with an antimicrobial carrier, excipient or diluent.

Where $R^3$ and $R^4$ are different the possibility of cis-/trans isomerism exists. It will be appreciated that both such forms of the compounds of formula I fall within the scope of the present invention.

According to one embodiment of the present invention we provide pharmaceutical and veterinary compositions containing as active ingredient a compound of the general formula

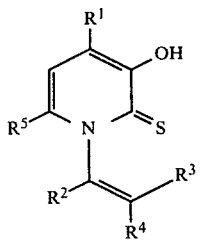

(I)

(where $R^1$ and $R^5$, which may be the same or different, each represent a hydrogen or halogen atom and $R^2$, $R^3$ and $R^4$ which may be the same or different, each represent a hydrogen atom or a lower alkyl group) in association with a pharmaceutical carrier or excipient. Bromine and chlorine are preferred halogens for the substituents $R^1$ and $R^5$.$R^5$, however, is preferably hydrogen. Lower alkyl substituents preferably have 1–5 carbon atoms, and may, for example be methyl, ethyl, isopropyl or butyl groups, a methyl group being preferred.

The new compounds possess an unusually broad spectrum of antifungal and antibacterial activity, being effective, for example, against *Staphylococcus aureus* as well as a range of fungi, such as *Candida albicans* and the dermatophytes *Penicillium patulum, Trichophyton mentagrophytes* and *Microsporum canis*.

The widely used antifungal agent tolnaftate has, in contrast, no antibacterial activity and is inactive against *Candida albicans*.

The new compounds thus make possible general purpose antifungal topical formulations in contrast to the previously used specialised antifungal preparations.

Particularly useful compounds as active ingredient are those in which (a) all of $R^1$, $R^2$, $R^3$, $R^4$ and $R^5$ represent hydrogen, or (b) $R^1$ represents a halogen atom while $R^2$, $R^3$, $R^4$ and $R^5$ represent hydrogen or (c) one of $R^2$, $R^3$ and $R^4$ represents a methyl group while the other two represent hydrogen and $R^1$ and $R^5$ represents hydrogen or (d) $R^1$, $R^2$, $R^3$ and $R^4$ represent hydrogen atoms and $R^5$ represents a chlorine atom. Especially noteworthy compounds thus include N-vinyl-3-hydroxy-pyrid-2-thione, N-vinyl-4-bromo or N-vinyl-4-chloro-3-hydroxy-pyrid-2-thione, N-prop-1'-en-1'-yl-3-hydroxy-pyrid-2-thione, N-prop-2-en-2-yl-3-hydroxy-pyrid-2-thione and N-vinyl-6-chloro-3-hydroxy-3-pyrid-2-thione.

The compositions according to the present invention may be formulated for application topically or by any other suitable route. Compositions for veterinary or human use could include general skin infections; pressure sprays for application either topically to the skin or to the mucous membranes of the nose, throat nd bronchii. For materials which show oral activity, forms of administration may be tablets, capsules or liquid preparations.

The various compositions may include additional active ingredients such as other antimicrobials and anti-inflammatory steroids e.g. hydrocortisone. Compositions may also include transfer mechanism agents such as dimethyl sulphoxide and materials which enhance or have a synergistic effect on the activity of the compounds of this invention.

Topical application is particularly advantageous and thus suitable formulations include creams, lotions and dusting powders.

Conventional or cosmetic bases may be employed for the preparation of ear drops, lotions, creams, hydrophobic and hydrophilic ointments etc. Nasal drops and pressure sprays for application to the mucous membranes of the nose, throat and bronchial tissues, may have the active ingredients dissolved or suspended in the bases, which may include non-toxic propellants for use in aerosol spray packs.

Conventional tabletting agents may include inert diluents and fillers such as starch, sugars, alcohols or mineral carriers; binding agent: such as syrup, acacia and cellulose derivatives; disintegrating agents e.g. potato starch and surfactants such as polyethylene glycols; lubricating materials e.g. magnesium stearate, talc, and finely dispersed silicon dioxide. Tablets may be engraved during compression for identification and/or coated by conventional processes such as sugar or film coating. Creams, ointments and lotions should suitably contain 0.2 to 5.0% by weight of the active ingredient of formula I, advantageously 0.5 to 2.0%. Aerosols should suitably contain 0.02 to 1% by weight, advantageously 0.05 to 0.5%; while dusting powders suitably contain 0.1 to 3.0%, advantageously about 1% by weight.

As stated above the compounds of formula I are also of potential interest as active ingredients in compositions for use against plant fungal pathogens such as mildew.

Thus in one embodiment of the present invention we provide agricultural compositions comprising as active ingredient at least one compound of formula I as hereinbefore defined in association with a non-phytotoxic carrier or diluent.

The new compounds according to the invention can be formulated for use in any desired way. Such formulations will include the compound in association with a non-phytotoxic carrier or diluent. Such carriers may be liquid or solid and designed to aid the application of the compound either by way of dispersing it where it is to be applied or to provide a formulation which can be made by the user into a dispersible preparation.

Liquid preparations thus include preparations of the compound in the form of emulsifiable concentrates, solutions or emulsions which can be used on their own or be adapted to be made up with water or other diluents to form sprays etc.; in such cases the carrier is a solvent or emulsion base non-phytotoxic under the conditions of use. Generally such preparations will include a wetting, dispersing or emulsifying agent. Other liquid preparations include aerosols in which the compound is associated with a liquid carrier or propellant.

Solid preparations include dusts and wettable powders, granulates and pellets, mordant powders, and semi-solid preparations such as pastes. Such preparations may include inert solid or liquid diluents such as clays, which may themselves have wetting properties, and/or wetting, dispersing or emulsifying agents; binding and/or adhesive agents may also be included. Solid preparations also include thermal fumigating mixtures wherein the compound is associated with a solid pyrotechnic component.

Compositions according to the present invention, in liquid form preferably contain from 0.01% to 5 especially from 0.05 to 1.0% by weight of active ingredient.

In ultra-low volume formulations and dusts higher active ingredient concentrations are, in general, used e.g. 5 to 15% by weight.

According to a further feature of the present invention there is provided a method of preventing or inhibiting the growth or proliferation of bacteria or fungi which comprises applying to a site to be protected against infection by bacteria or fungi or already infected by bacteria or fungi an effective amount of a pharmaceutical or veterinary composition as hereinbefore defined.

We also provide a method of preventing or inhibiting the growth or proliferation of mildew which comprises applying to a site to be protected against infestation by mildew or already infested by mildew an effective amount of an agricultural composition as hereinbefore defined.

Many of the compounds of the formula I are novel compounds constituting a further feature of the present invention, namely compounds of the general formula I as defined above in which $R^1$, $R^2$ and $R^5$ do not all represent hydrogen atoms when either one of $R^3$ and $R^4$ represents a hydrogen atom while the other represents a methyl group or both $R^3$ and $R^4$ represents a hydrogen atom. The compounds in which $R^1$, $R^2$ and $R^5$ are all hydrogen and either one of $R^3$ and $R^4$ is hydrogen while the other is methyl or both $R^3$ and $R^4$ are hydrogen have only been described previously in relation to chemical investigations and their possible utility in medicine or, indeed, any other utility has not been suggested. Preferred compounds according to the present invention, by virtue of their antimicrobial activity, include the following:

N-vinyl-4-bromo-3-hydroxy-pyrid-2-thione,
N-vinyl-4-chloro-3-hydroxy-pyrid-2-thione,
N-prop-2'-en-2'-yl-3-hydroxy-pyrid-2-thione and
N-vinyl-6-chloro-3-hydroxy-pyrid-2-thione.

Furthermore, the two compounds in which $R^1$, $R^2$ and $R^5$ are all hydrogen and one of $R^3$ and $R^4$ is methyl while the other is hydrogen, namely cis- and trans-N-prop-1'-en-1'-yl-3-hydroxy-pyrid-2-thione have only been described in admixture and the separate isomers constitute a further feature of the invention.

We have also found a novel process for the preparation of compounds of the general formula I and this constitutes a still further feature of the present invention.

The process according to the invention comprises reaction of a compound of the general formula

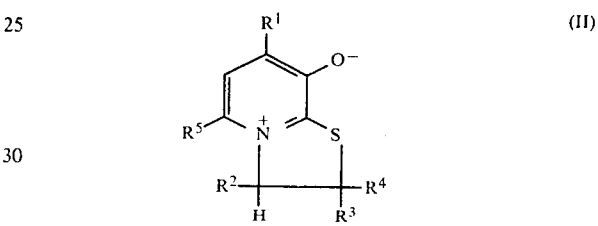

(II)

or an acid addition salt thereof (where $R^1$, $R^2$, $R^3$, $R^4$ and $R^5$ are as defined for formula I above) with a base whereby the proton adjacent to $R^2$ is abstracted and the dihydrothiazolo ring is opened. The acid addition salts may be formed, for example, with mineral acids such as hydrohalic acids, e.g. hydrogen bromide or hydrogen chloride.

In this reaction, when $R^3$ and $R^4$ are different, a compound in which the pyridine ring is trans to the larger of $R^3$ and $R^4$ is the generally favoured product.

Suitable bases include lithium alkyls such as lithium t-butyl and lithium-nitrogen derivatives such as lithium diisopropylamide; alkali metals in liquid ammonia or a liquid amine; alkali metal hydroxides and alkali metal oxides. The anion of the base is preferably bulky to avoid or reduce nucleophilic attack. A reagent of choice generally applicable in all cases is an alkali metal t-butoxide, especially potassium t-butoxide.

The reaction is conveniently effected:

a polar solvent such as dialkylformamide or dialkylacetamide or a tertiary alcohol, e.g. t-butanol or the reaction medium can comprise an excess of the base medium, e.g. ammonia or an amine. The reaction proceeds well at ambient temperature and yields of 70-80% may be obtained.

The new compounds according to the present invention may also be prepared by any other convenient method, in particular by pyrolytic decarboxylation under anhydrous conditions of compounds of the general formula

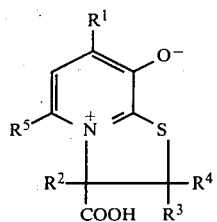

where $R^1$-$R^5$ are as defined above and $R^1$, $R^2$ and $R^5$ do not all represent hydrogen atoms when either one of $R^3$ and $R^4$ represents a hydrogen atom while the other represents a methyl group or both $R^3$ and $R^4$ represent a hydrogen atom or an alkyl group, or a salt thereof. The pyrolysis is advantageously effected at a temperature of from 150°-180° C. at reduced pressure. The starting material is conveniently ground together with quartz sand or, in the case of a salt with a strong acid, an anhydrous alkali metal carbonate, e.g. potassium carbonate.

Where $R^3$ and $R^4$ are different, a mixture of cis and trans isomers is obtained in this reaction.

Both cis and trans isomers possess activity.

The dihydrothiazolo[3,2-a]pyridinium starting materials of formulae II and III may be prepared by methods known in the chemical literature, e.g. by reaction of a pyrid-2-thione with a 1,2-dihaloalkane or 1,2-dihaloalkanoic acid, or a 2-halopyridine with a 1-halo-2-mercapto alkane or -alkanoic acid. $R^1$ and $R^5$ when halogen atoms, may be introduced by halogenation of the product of such a reaction.

The following Examples illustrate the invention further.

PREPARATION OF STARTING MATERIALS

5,7-Dibromodihydrothiazolo[3,2-a]pyridinium-8-oxide hydrobromide

Bromine (16.0 g, 0.10 mole) in methanol (100 ml) was added dropwise at room temperature to a solution of dihydrothiazolo[3,2-a]pyridinium-8-oxide hydrobromide (11.85 g, 0.05 mole) in methanol (200 ml). The precipitated product was collected the next day; yield 12.0 g (66%), m.p. 280° C. (decom.). The product was recrystallised from aq. HBr for elemental analysis. (Found: C 20.62; H 2.10 Calcd. for $C_7H_5Br_2NOS$. $HBr.H_2O$: C 20.47; H 1.95); $\tau$ (TFA) 6.0 (S-$CH_2$), 4.6 (N-$CH_2$), 2.0 (H-6).

7-Bromodihydrothiazolo[3,2-a]pyridinium-8-oxide hydrobromide

Bromine (4.8 g, 0.03 mole) in methanol (70 ml) at −70° C. was added dropwise over 10 h to a solution of dihydrothiazolo[3,2-a]pyridinium-8-oxide hydrobromide (7.0 g, 0.03 mole) in methanol (600 ml) at −70° C. The solution was then allowed to reach room temperature and evaporated. The residual material was recrystallized three times from small volumes of water; yield: 3.0 g (32%); m.p. 245° C. (decomp.). (Found: C 26.84; H 2.61; Calcd. for $C_7H_6BrNOS$. HBr; C 26.86; H 2.25); $\tau$ (TFA) 6.1 (S-$CH_2$), 4.8 (N-$CH_2$), 2.3 and 1.9 (pyridine, AB, J=6.5 Hz).

7-Chlorodihydrothiazolo[3,2-a]pyridinium-8-oxide hydrobromide

A solution of 7-bromodihydrothiazolo[3,2-a]pyridinium-8-oxide (2.0 g, 0.006 mole) in DMF (175 ml) at 90° C. was saturated with sodium chloride and kept at this temperature for 4 h. The solution was then allowed to cool to room temperature and the precipitated salt removed before evaporation at reduced pressure of the filtrate. The residue was triturated with ether and recrystallized from a small volume of water; yield: 0.9 g (63%); m.p. >270° C. (decomp.). (Found: C 31.22; H 2.88. Calcd. for $C_7H_6Cl$ NOS.HBr C 31.20; H 2.66) $\tau$ (TFA) 6.1 (S-$CH_2$), 4.8 (N-$CH_2$), 2.4 and 1.8 (pyridine, AB, J=6.5 Hz).

5,7-Dichlorodihydrothiazolo[3,2-a]pyridinium-8-oxide (a) hydrobromide:

The title compound was prepared in the same way as the 7-chloro derivative above; 5,7-dibromodihydrothiazolo [3,2-a]pyridinium-8-oxide hydrobromide in DMF saturated with sodium chloride was heated at 90° C. for 4 hr. The product was worked up as above and recrystallised from water; Yield 55%, m.p. 275° C. (decomp.). (Found: C 27.58; H 2.07. Calc. for $C_7H_5Cl_2NOS.HBr$: C 27.81; H 1.98) $\tau$ (TFA) 6.0 (S-$CH_2$), 4.7 (N-$CH_2$), 2.4 (pyridine singlet).

(b) betaine:

5-Chloro-7-nitrodihydrothiazolo[3,2-a]pyridinium-8-oxide was prepared from 5-chlorodihydrothiazole[3,2-a]pyridinium-8-oxide (5.0 g, 0.03 mol) dissolved in acetic acid (100 ml) by the dropwise addition of a solution of fuming nitric acid (5 ml) and concentrated sulphuric acid (4 ml) in acetic acid (50 ml) with stirring at room temperature. The reddish precipitate of 5-chloro-7-nitrodihydrothiazolo[3,2-a]pyridinium-8-oxide was recrystallized from ethanol; yield 60%, m.p. 180°-190° C. (decomp.) (Found: C 36.11; H 2.46. Calc. for $C_7H_5ClN_2O_3S$: C 36.20; H 2.16) $\tau$ (TFA) 5.9 (S—$CH_2$), 4.5 (N—$CH_2$), 1.85 (H-pyridine).

The 5,7-dichloro derivative was prepared by heating under reflux a solution of 5-chloro-7-nitrodihydrothiazolo [3,2-a]pyridinium-8-oxide (1.1 g, 0.005 mol) and zinc chloride (2.0 g) in 3 N HCl (50 ml) for 3 days. The solution was then evaporated, the residue dissolved in water and the aqueous solution neutralized with NaOH before being passed through a cation exchange column (IR-120 Amberlite in $H^+$-form). The chloride ions were removed by elution with water, and the desired substance was eluted with 0.6 N aq. ammonia. Evaporation of the $NH_3$-eluates left the betaine; yield 78%, m.p. 220°-2225° C. (decomp.). The identity of the compound was verified by spectroscopic and chromatographic comparison with the hydrobromide synthesized according to (a).

5-Chlorodihydrothiazolo[3,2-a]pyridinium-8-oxide hydrochloride

Dihydrothiazolo[3,2-a]pyridinium-8-oxide (0.45 g., 0.003 mol) was dissolved in DMF (1.5 ml) and the solution cooled to −60° C. Sulphuryl chloride (1.0 ml) was then added dropwise to this solution at 60° with stirring. When the addition was completed, the reaction mixture was slowly allowed to reach room temperature overnight. Addition of a little water to the reaction mixture was followed by evaporation under reduced pressure to a small volume. The title compound crystallized out from the solution in 48% yield (0.32 g.); the sample for elemental analysis was recrystallized from a small volume of water, m.p. 270° C. (decomp.). (Found: C 37.41; H 3.19. Calc. for $C_7H_6ClNOS.HCl$: C 37.50; H 3.12); τ (TFA) 6.1 (S—CH$_2$), 4.7 (N—CH$_2$), 2.6 and 2.3 (pyridine, AB, J=8.5 Hz).

EXAMPLE 1

N-Vinyl-3-hydroxypyrid-2-thione (a) DMF-solvent:

A solution of 0.5 M potassium tert.-butoxide in tert.-butanol (75 ml, 0.038 mole) was added dropwise over 3 h at room temperature to a stirred solution of dihydrothiazolo[3,2-a]pyridinium-8-oxide (4.6 g, 0.03 mole) in DMF (400 ml). Acetic acid was then added until acid pH and the reaction mixture evaporated at reduced pressure. The residual material was triturated with water (20 ml) and the insoluble title material filtered off; yield 3.2 g. (70%).

(b) tert.-Butanol solvent:

Dihydrothiazolo[3,2-a]pyridinium-8-oxide (13.8 g., 0.09 mole) was added to 0.5 M potassium tert.-butoxide in tert.-butanol (450 ml, 0.23 mole) and the reaction mixture stirred at room temperature overnight. Acetic acid (13 ml) was then added until acid pH and the reaction mixture evaporated at reduced pressure. The residual material was triturated with water (35 ml) and the insoluble title compound collected by filtration; yield 9.7 g. (70%), m.p. 84° C. (EtOH). (Found: C 55.09; H 4.83 Calcd. for C$_7$H$_7$NOS: C 54.90; H 4.61). τ 4.7 (J=8.5 Hz) and 4.5 (J=16 Hz; =CH$_2$, J$_{gem}$=2 Hz), 2.1 (CH-N) 2.3-2.5 and 3.0 and 3.4 (pyridine); λ$_{max}$(EtOH) 378 (log ε3.97). 274 sh. (3.80) and 261 nm (3.81).

TLC on silica gel:

n-BuOH: EtOH 0.88NH$_3$ (8:2:1) R$_f$=0.55-0.6
PhMe:MeCN:HOAc (10:10:1) R$_f$=0.8-0.85
n - BuOH: EtOH (4:1) R$_f$=0.65

EXAMPLE 2

N-Vinyl-4 6-dibromo-3-hydroxypyrid-2-thione

Using the method of Example 1(a) a solution of 0.5 M potassium tert.-butoxide in tert.-butanol (0.004 mole, 8 ml) was added dropwise over 8 min. to a solution of 5,7-dibromodihydrothiazolo[3,2-a]pyridinium-8-oxide (0.79 g. 0.002 mole) in DMF (200 ml) at room temperature. The reaction mixture was left for another 20 min. before addition of acetic acid until acid pH. The mixture was then evaporated at reduced pressure. The residue was triturated with water and the vinyl pyridine extracted into ether. Drying and evaporation of the ethereal solution left the title compound which was further purified by recrystallization from methanol: yield 0.47 g. (76%) m.p. 134° C. (MeOH); (Found C 27.17; H 1.85. Calcd. for C$_7$H$_5$Br$_2$NOS: C 27.03; H 1.62); τ4.7 (J=16 Hz) and 4.3 (J=8 Hz; =CH$_2$, J$_{gem}$ 1.5 Hz) 3.3 (CH-N), 2.8 (pyridine).

EXAMPLE 3

N-Vinyl-4-bromo-3-hydroxypyrid-2-thione

In a manner analogous to Example 1(a) 7-bromodihydrothiazolo[3,2-a]pyridinium-8-oxide gave the above compound (79%) m.p. 127°-128° C. (MeOH). (Found: C 36.36; H 2.68. Calcd. for C$_7$H$_6$BrNOS: C 36.22; H 2.61); τ(CDCl$_3$) 4.6 (J=8.5 Hz) and 4.5 (J=16 Hz; =CH$_2$, J$_{gem}$=2 Hz), 2.3 (N—CH=), 3.1 and 2.7 (pyridine, AB, J=7 HZ).

EXAMPLE 4

N-Vinyl-4-chloro-3-hydroxypyrid-2-thione

In a manner analogous to Example 1(a), 7-chlorodihydrothiazolo[3,2a]pyridinium-8-oxide gave the above compound (67%) m.p. 132° C. (MeOH). (Found: C 44.57; H 3.16;) Calcd. for C$_7$H$_6$ClNOS: C 44.78; H 3.20);τ(CDCl$_3$) 4.7 (J=8.5 Hz) and 4.6 (J=16 Hz, =CH$_2$, J$_{gem}$=1.5 Hz), 2.3 (N—CH=), 3.3 and 2.7 (pyridine, AB, J=7 Hz).

EXAMPLE 5

N-Prop-1-en-1-yl-3-hydroxypyrid-2-thione

By the method of Example 1(a), 2-methyl-dihydrothiazolo [3,2-a]pyridinium-8-oxide gave the above compound (yield 68%), m.p. 98°-100° C. (MeOH). (Found: C 57.45; H 5.10. Calc. for C$_8$H$_9$NOS: C 57.48; H 5.43%)τ(CDCl$_3$) 8.1 (Me, J=7.0 and 1.5 Hz), 4.1 (=CH—Me), 3.3 (N—CH=, J=14). According to NMR the product has trans configuration.

EXAMPLE 6

N-Vinyl-6-chloro-3-hydroxypyrid-2-thione

In a manner analogous to Example 1(a) 5-chlorodihydrothiazolo[3,2a]-pyridinium-8-oxide gave the above compound together with the S-vinyl analogue in 59% yield; 10-15% of the product are the vinylthio isomer. The isomers are separated by crystallisation from methanol; the title compound crystallised out in yields corresponding to 60-70% of the crude vinyl product.

The remaining mixture of the N-vinyl and S-vinyl isomers in the methanol filtrate can be separated on a silica gel column packed in N-BuOH: EtOH (4:1). The S-vinyl isomer is initially eluated.

M.p. for the title compound 100° C. (Found: C 44.89; H 3.43. Calc. for C$_7$H$_6$ClNOS: C 44.78; H 3.20); τ(CDCl$_3$) 4.6 (J=16 Hz) and 4.2 (J=8 Hz; CH$_2$=, J$_{vic}$=1.5 Hz), 3.1 (N—CH=), 3.3 and 3.1 (pyridine, AB).

EXAMPLE 7

N-Vinyl-4,6-dichloro-3-hydroxypyrid-2-thione

In a manner analogous to Example 1 (a) 5,7-dichlorodihydrothiazolo[3,2-a]-pyridinium-8-oxide gave the title compound together with the S-vinyl analogue in 55% yield; 10-15% of the product are the S-vinyl isomer. The isomers are separated by crystallisation from methanol; the title compound crystallised out in yields corresponding to 60-70% of the crude vinyl product. M.p. 114° C. (Found: C 37.08; H 2.36. Calc. for C$_7$H$_5$Cl$_2$NOS: 37.85; H 2.25); τ(CDCl$_3$) 4.6 (J=16 Hz) and 4.2 (J=8 Hz; CH$_2$=, J$_{gem}$=1.5 Hz), 3.2 (N—CH=), 3.1 (pyridine singlet).

EXAMPLE 8

N-Prop-2-en-2-yl-3-hydroxypryid-2-thione

Reaction of 3-methyldihydrothiazolo[3,2-a]pyridinium-8-oxide as before gave a mixture of isomers which was separated by fractional crystallisation from chloroform when the unwanted thioether was selectively precipitated. Evaporation of the mother liquor and crystallisation of the residue from methanol gave the N-prop-2-en-2-yl isomer, m.p. 93° C. (Found: C 57.35; H 5.24. Calcd. for C$_8$H$_9$NOS: C 57.48; H 5.43); τ 7.7 (Me), 4.9 and 4.8 (J=1 Hz) (=CH$_2$, J$_{gem}$ <1 Hz); λ$_{max}$(EtOH)373 (log ε 4.06), 280 nm (3.7).

EXAMPLE 9

N-Vinyl-3-hydroxy-6-isopropylpyrid-2-thione

Reaction of 5-isopropyldihydrothiazolo[3,2-a]pyridinium-8-oxide as before gave the above compound in a yield of 37.0%. The product was isolated by chromatography on silica gel eluting with n-butanol/ethanol (4:1). The desired product was eluted last; m.p. 72° C. (Found: C 61.17; H 6.88; Calcd. for $C_{10}H_{13}NOS$: C 61.52; H 6.71); $\tau$ 8.8 and 6.7 (iPr), 4.7 (J=16 Hz) and 4.3 (J=8 Hz) (=CH$_2$, $J_{gem}$=1) 3.2 (CH—N), 3.0 and 3.4 (pyridine, J=8 Hz); $\lambda_{max}$(EtOH)372 (log $\epsilon$ 4.08) and 277 nm (3.70).

EXAMPLE 10—PROPYLENE GLYCOL BASED CREAM

|  | %w/w |
|---|---|
| N-vinyl-3-hydroxypyrid-2-thione | 1.0 |
| Cetostearyl alcohol | 35.0 |
| Propylene glycol | 58.5 |
| Water to | 100.0 |

EXAMPLE 11—POLYETHYLENE GLYCOL BASED OINTMENT

|  | %w/w |
|---|---|
| N-vinyl-4-chloro-3-hydroxypyrid-2-thione | 1.0 |
| Polyethylene glycol 4000 to | 20.0 |
| Polyethylene glycol 400 | 100.0 |

EXAMPLE 12—LOTION

|  | %w/w |
|---|---|
| N-vinyl-4-bromo-3-hydroxypyrid-2-thione | 1.0 |
| Methyl parahydroxybenzoate | 0.15 |
| Lanbritol wax | 0.93 |
| Diethylene glycol monostearate | 0.65 |
| Cetostearyl alcohol | 0.65 |
| Liquid paraffin | 1.95 |
| Cetomacrogol 1000 | 0.003 |
| Glycerine | 5.0 |
| Isopropyl alcohol | 6.5 (v/v) |
| Citric acid | 0.008 |
| Distilled water to | 100.0 |

EXAMPLE 13—DUSTING POWDER

|  | % w/w |
|---|---|
| N-propenyl-3-hydroxypyrid-2-thione | 1.0 |
| Maize starch | 49.4 |
| Aerosil | 0.15 |
| Purified talc to | 100.0 |

EXAMPLE 14—AEROSOL PREPARATION

|  | % w/w |
|---|---|
| N-vinyl-3-hydroxypyrid-2-thione | 0.1 |
| Arachis oil | 10.0 |
| Isopropyl alcohol | 10.0 |
| Trichlorofluoromethane (Freon 11) | 40.0 |
| Dichlorodifluoromethane (Freon 12) to | 100.0 |
| Pressure at 25° C. | 2.2 Kg/cm$^2$ |

EXAMPLE 15—ANTI-MILDEW CONCENTRATE

|  | % w/w |
|---|---|
| N-vinyl-3-hydroxypyrid-2-thione | 10 |
| Polyethylene glycol (Macrogol 400) | 90 |

A 0.1% aqueous solution for treating mildew was prepared by diluting the above-mentioned 10% solution in Macrogol 400 with water until the desired 0.1% aqueous solution was obtained.

We claim:

1. A pharmaceutical antimicrobial composition comprising as active ingredient at least one compound of the formula

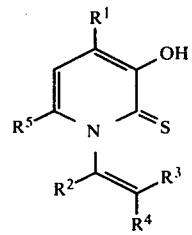

wherein $R^1$ and $R^5$, which may be the same or different each represent a hydrogen or halogen atom and $R^2$, $R^3$ and $R^4$ which may be the same or different, each represent a hydrogen atom or a lower alkyl group in association with a carrier, excipient or diluent therefor.

2. The pharmaceutical composition as claimed in claim 1, which comprises as active ingredient a compound of formula I as defined in claim 1 wherein $R^1$ and/or $R^5$ represents a hydrogen, chlorine or bromine atom.

3. The pharmaceutical composition as claimed in claim 1, which comprises as active ingredient N-vinyl-3-hydroxy-pyrid-2-thione.

4. The pharmaceutical composition as claimed in claim 1 which comprises as active ingredient a compound of formula I as defined in claim 1 wherein $R^1$ represents a halogen atom and $R^2$, $R^3$, $R^4$ and $R^5$ each represent a hydrogen atom.

5. The pharmaceutical composition as claimed in claim 1 which comprises as active ingredient N-vinyl-4-bromo-3-hydroxy-pyrid-2-thione, N-vinyl-4-chloro-3-hydroxy-pyrid-2-thione, N-prop-1'-en-1'-yl-3-hydroxy-pyrid-2-thione, N-prop-2'-en-2'-yl-3-hydroxy-pyrid-2-thione or N-vinyl-6-chloro-3-hydroxy-pyrid-2-thione.

6. The pharmaceutical composition as claimed in claim 1 in a form suitable for oral, topical, nasal or aural administration.

7. The pharmaceutical composition as claimed in claim 1 in the form of creams, ointments and lotions which contain 0.2 to 5.0% by weight of the active ingredient of formula I.

8. The pharmaceutical composition as claimed in claim 1 in the form of an aerosol spray containing 0.02 to 1% by weight of the active ingredient of formula I.

9. The pharmaceutical composition as claimed in claim 1 in the form of dusting powders which contain 0.1 to 3.0% by weight of the active ingredient of formula I.

10. The pharmaceutical composition as claimed in claim 1 which further contains an antimicrobial or anti-inflammatory steroid.

11. A veterinary antimicrobial composition comprising as active ingredient at least one compound of the formula

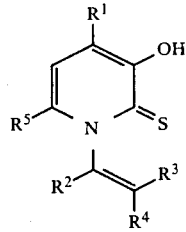

I wherein $R^1$ and $R^5$, which may be the same or different each represent a hydrogen or halogen atom and $R^2$, $R^3$ and $R^4$ which may be the same or different, each represent a hydrogen atom or a lower alkyl group in association with a carrier, excipient or diluent therefor.

12. The veterinary composition as claimed in claim 11 which comprises as active ingredient a compound of formula I as defined in claim 11, wherein $R^1$ and/or $R^5$ represent a hydrogen, chlorine or bromine atom.

13. The veterinary composition as claimed in claim 11 which comprises as active ingredient N-vinyl-3-hydroxy-pyrid-2-thione.

14. The composition as claimed in claim 11 which comprises as active ingredient a compound of formula I as defined in claim 11 wherein $R^1$ represents a halogen atom and $R^2$, $R^3$, $R^4$ and $R^5$ each represent a hydrogen atom.

15. The veterinary composition as claimed in claim 11 which comprises as active ingredient N-vinyl-4-bromo-3-hydroxy-pyrid-2-thione, N-vinyl-4-chloro-3-hydroxy-pyrid-2-thione, N-prop-1'-en-1'-yl-3-hydroxy-pyrid-2-thione, N-prop-2'-yl-3-hydroxy-pyrid-2-thione or N-vinyl-6-chloro-3-hydroxy-pyrid-2-thione.

16. The veterinary composition as claimed in claim 11 in a form suitable for oral, topical, nasal or aural administration.

17. The veterinary composition as claimed in claim 11 in the form of creams, ointments and lotions which contain 0.2 to 5.0% by weight of the active ingredient of formula I.

18. The veterinary composition as claimed in claim 11 in the form of an aerosol spray containing 0.02 to 1% by weight of the active ingredient of formula I.

19. The veterinary composition as claimed in claim 11 in the form of dusting powders which contain 0.01 to 3.0% by weight of the active ingredient of formula I.

20. The veterinary composition as claimed in claim 11 which further contains an antimicrobial or anti-inflammatory steroid.

21. An agricultural antimicrobial composition comprising as active ingredient at least one compound of the general formula

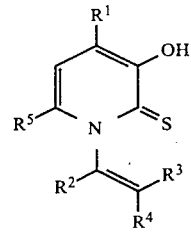

I wherein $R^1$ and $R^5$, which may be the same or different, each represent a hydrogen or halogen atom and $R^2$, $R^3$ and $R^4$, which may be the same or different, each represent a hydrogen atom or a lower alkyl group in association with a non-phytotoxic carrier, or diluent.

22. The agricultural composition as claimed in claim 21 which comprises as active ingredient a compound of formula I as defined in claim 21 wherein $R^1$ and/or $R^5$ represents a hydrogen, chlorine or bromine atom.

23. The agricultural composition as claimed in claim 21 which comprises as active ingredient N-vinyl-3-hydroxy-pyrid-2-thione.

24. The agricultural composition as claimed in claim 21 which comprises as active ingredient a compound of formula I as defined in claim 21 wherein $R^1$ represents a halogen atom and $R^2$, $R^3$, $R^4$ and $R^5$ each represent a hydrogen atom.

25. The agricultural composition as claimed in claim 21 in the form of solutions, emulsifiable concentrates, wettable powders, dusts, mordant powders, granules, aerosols, sprays or thermal fumigating mixtures in which the active ingredient is associated with a solid pyrotechnic component.

26. The agricultural composition as claimed in claim 21 in liquid form, in which the concentration of active ingredient is from 0.01 to 5.0% by weight or in the form of ultra-low volume compositions and dusts which contain 5 to 15% by weight of active ingredient.

27. A method of preventing or inhibiting the growth or proliferation of bacteria or fungi which comprises applying to a site to be protected against infection by bacteria or fungi or already infected by bacteria or fungi an effective amount of a pharmaceutical composition as claimed in claim 1.

28. A method of preventing or inhibiting the growth or proliferation of bacteria or fungi which comprises applying to a site to be protected against infection by bacteria or fungi or already infected by bacteria or fungi, an effective amount of a veterinary composition as claimed in claim 11.

29. A method of preventing or inhibiting the growth or proliferation of mildew which comprises applying to a site to be protected against infection by mildew or already inested by mildew an effective amount of an agricultural composition as claimed in claim 21.

30. A compound having the formula:

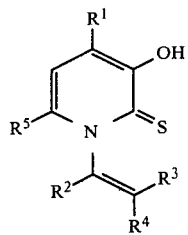

where $R^1$ and $R^5$, which may be the same or different each represent a hydrogen or halogen atom and $R^2$, $R^3$ and $R^4$ which may be the same or different, each represent a hydrogen atom or a lower alkyl group, with the proviso that $R^1$, $R^2$ and $R^5$ do not all represent hydrogen atoms when either one of $R^3$ and $R^4$ represents a hydrogen atom while the other represents a methyl group or both $R^3$ and $R^4$ represent a hydrogen atom.

31. The compound as claimed in claim 30, which is a compound selected from the group consisting of N-vinyl-4-bromo-3-hydroxy-pyrid-2-thione, N-vinyl-4-chloro-3-hydroxypyrid-2-thione, N-prop-2'-en-2'-yl-3-hydroxy-pyrid-2-thione, and N-vinyl-6-chloro-3-hydroxy-pyrid-2-thione.

32. The compound as claimed in claim 30 which is trans-N-prop-1'-en-1'-yl-3-hydroxy-pyrid-2-thione substantially free from the cis-isomer thereof.

* * * * *